US00PP34743P2

(12) United States Plant Patent
Beers

(10) Patent No.: US PP34,743 P2
(45) Date of Patent: Nov. 15, 2022

(54) ***GERBERA* PLANT NAMED 'MAJBUR20AA'**

(50) Latin Name: *Gerbera hybrida*
Varietal Denomination: MAJBUR20AA

(71) Applicant: HilverdaFlorist B.V., De Kwakel (NL)

(72) Inventor: Martin Beers, Hoofddorp (NL)

(73) Assignee: HilverdaFlorist B.V., De Kwakel (NL)

( * ) Notice: Subject to any disclaimer, the term of this patent is extended or adjusted under 35 U.S.C. 154(b) by 0 days.

(21) Appl. No.: 17/747,730

(22) Filed: May 18, 2022

Related U.S. Application Data

(60) Provisional application No. 63/192,017, filed on May 22, 2021.

(51) Int. Cl.
*A01H 5/02* (2018.01)
*A01H 6/14* (2018.01)

(52) U.S. Cl.
USPC ..... Plt./357

(58) Field of Classification Search
USPC ..... Plt./263.1, 357
See application file for complete search history.

(56) References Cited

PUBLICATIONS

Wilson Bros Gardens citation for 'Sweet Suprise' Gerbera Daisy, https://www.wilsonbrosgardens.com/gerbera-jamesonii-garvinea-sweet-surprise-gerber-daisy-1-gallon.html. 6 pages. (Year: 2022).*

* cited by examiner

*Primary Examiner* — Karen M Redden
(74) *Attorney, Agent, or Firm* — C. Anne Whealy

(57) ABSTRACT

A new and distinct cultivar of *Gerbera* plant named 'MAJBUR20AA', characterized by its broadly upright and uniformly mounding plant habit; moderately vigorous to vigorous growth habit; dense and bushy appearance; numerous inflorescences with deep red purple-colored ray florets; upright and moderately strong peduncles; good garden performance and relative tolerance to low temperatures.

1 Drawing Sheet

Botanical designation: *Gerbera hybrida.*
Cultivar denomination: 'MAJBUR20AA'.

BACKGROUND OF THE INVENTION

The present invention relates to a new and distinct cultivar of *Gerbera* plant, botanically known as *Gerbera hybrida* and hereinafter referred to by the cultivar name 'MAJBUR20AA'.

The new *Gerbera* plant is a product of a planned breeding program conducted by the Inventor in De Kwakel, The Netherlands. The objective of the breeding program is to create new garden *Gerbera* plants with numerous attractive inflorescences, resistant to cold temperatures and good garden performance.

The new *Gerbera* plant originated from a cross-pollination in March, 2014 of a proprietary selection of *Gerbera hybrida* identified as code number 14T1407, not patented, as the female, or seed, parent with a proprietary selection of *Gerbera hybrida* identified as code number 15T1531, not patented, as the male, or pollen, parent. The new *Gerbera* plant was discovered and selected as a single flowering plant from within the progeny of the stated cross-pollination in a controlled greenhouse environment in De Kwakel, The Netherlands in June, 2015.

Asexual reproduction of the new *Gerbera* plant by vegetative terminal cuttings and in vitro meristem culture in De Kwakel, The Netherlands since August, 2015 has shown that the unique features of this new *Gerbera* plant are stable and reproduced true to type in successive generations of asexual reproduction.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MAJBUR20AA'. These characteristics in combination distinguish 'MAJBUR20AA' as a new and distinct *Gerbera* plant:

1. Broadly upright and uniformly mounding plant habit.
2. Moderately vigorous to vigorous growth habit.
3. Dense and bushy appearance.
4. Numerous inflorescences with deep red purple-colored ray florets.
5. Upright and moderately strong peduncles.
6. Good garden performance and relative tolerance to low temperatures.

Plants of the new *Gerbera* differ primarily from plants of the female parent selection in the following characteristics:

1. Plants of the new *Gerbera* have larger inflorescences with larger ray florets than plants of the female parent selection.
2. Plants of the new *Gerbera* have deep red purple-colored ray florets whereas plants of the female parent selection have light red-colored ray florets.

Plants of the new *Gerbera* differ primarily from plants of the male parent selection in the following characteristics:

1. Plants of the new *Gerbera* have shorter and narrower leaves than plants of the male parent selection.
2. Plants of the new *Gerbera* have deep red purple-colored ray florets whereas plants of the male parent selection have dark pink-colored ray florets.
3. Plants of the new *Gerbera* have shorter peduncles than plants of the male parent selection.

Plants of the new *Gerbera* can be compared to plants of the *Gerbera hybrida* 'MAJPUR21AA', disclosed in a U.S. Plant patent application Ser. No. 17/747,755 filed concurrently. In side-by-side comparisons, plants of the new *Gerbera* differ from plants of 'MAJPUR21AA' in the following characteristics:

1. Plants of the new *Gerbera* have longer and broader leaves smaller inflorescences than plants of 'MAJPUR21AA'.
2. Plants of the new *Gerbera* have larger inflorescences than plants of 'MAJPUR21AA'.
3. Ray florets of plants of the new *Gerbera* are darker red purple in color than ray florets of plants of 'MAJPUR21AA'.
4. Plants of the new *Gerbera* have longer peduncles than plants of 'MAJPUR21AA'.

BRIEF DESCRIPTION OF THE PHOTOGRAPH

The accompanying photograph illustrates the overall appearance of the new *Gerbera* plant showing the colors as true as it is reasonably possible to obtain in colored reproductions of this type. Colors in the photograph may differ slightly from the color values cited in the detailed botanical description which accurately describe the colors of the new *Gerbera* plant. The photograph is a side perspective view of a typical flowering plant of 'MAJBUR20AA' grown in a container.

DETAILED BOTANICAL DESCRIPTION

The aforementioned photograph and following observations and measurements describe plants grown during the winter and early spring in 19-cm containers in a glass-covered greenhouse in De Kwakel, The Netherlands and under cultural practices typical of commercial garden *Gerbera* production. During the production of the plants, day and night temperatures ranged from 12° C. to 16° C. Plants were six months old when the photograph was taken and 20 weeks old when the description was taken. In the following description, color references are made to The Royal Horticultural Society Colour Chart, 2015 Edition, except where general terms of ordinary dictionary significance are used.

Botanical classification: *Gerbera hybrida* 'MAJBUR20AA'.

Parentage:

*Female, or seed, parent*.—Proprietary selection of *Gerbera hybrida* identified as code number 14T1407, not patented.

*Male, or pollen, parent*.—Proprietary selection of *Gerbera hybrida* identified as code number 15T1531, not patented.

Propagation:

*Type*.—By cuttings and in vitro meristem culture.

*Time to initiate roots, by cuttings, summer and winter*.—About 3.5 weeks at minimum temperatures of 20° C.

*Time to initiate roots, by tissue culture, summer and winter*.—About 2.5 to 3 weeks at minimum temperatures of 20° C.

*Time to produce a rooted young plant, by cuttings, summer and winter*.—About 3.5 weeks after rooting, at temperatures about 20° C. to 26° C.

*Time to produce a rooted young plant, by tissue culture, summer and winter*.—About five to six weeks at temperatures about 20° C. to 26° C.

*Root description*.—Fibrous; typically white in color, actual color of the roots is dependent on substrate composition, water quality, fertilizer type and formulation, substrate temperature and physiological age of roots.

Plant description:

*Appearance*.—Herbaceous perennial that is typically grown as a container or garden plant; broadly upright and uniformly mounding plant habit; roughly flattened globular in shape; numerous leaves arranged in basal rosettes; dense and bushy habit; inflorescences held above the foliar plane on erect and strong basal peduncles; moderately vigorous to vigorous growth habit and moderate growth rate.

*Plant height, soil level to top of foliar plane*.—About 31.2 cm.

*Plant height, soil level to top of inflorescences*.—About 45 cm.

*Plant width or spread*.—About 64.2 cm.

Leaf description:

*Arrangement*.—Alternate, basal, simple.

*Length*.—About 22.2 cm.

*Width*.—About 9.5 cm.

*Shape*.—Narrowly ovate to narrowly oblong.

*Apex*.—Obtuse.

*Base*.—Broadly attenuate.

*Margin*.—Coarsely and shallowly repand to coarsely and shallowly angulate or entire; proximally, coarsely and irregularly angulate to runcinate; sinuses deep and parallel.

*Texture and luster, upper surface*.—Sparsely pubescent; slightly rugose; moderately glossy.

*Texture and luster, lower surface*.—Moderately to densely pubescent; matte.

*Venation pattern*.—Pinnate.

*Color*.—Developing leaves, upper surface: Close to a blend of 141A and 143A. Developing leaves, lower surface: Close to a blend of 138A and 147B. Fully expanded leaves, upper surface: Close to NN137B; venation, close to 144A. Fully expanded leaves, lower surface: Close to a blend of 147C and 148B; venation, close to 146C.

*Petioles*.—Length: About 13 cm. Diameter: About 4 mm. Texture and luster, upper and lower surfaces: Moderately to densely pubescent; slightly glossy. Strength: Moderately strong to strong. Color, upper and lower surfaces: Close to 144A.

Inflorescence description:

*Appearance*.—Composite inflorescence form with oblanceolate-shaped ray florets; solitary inflorescences borne on upright and moderately strong peduncles and held above the foliar plane; ray and disc florets arranged acropetally on a capitulum; inflorescences face upright.

*Fragrance*.—None detected.

*Flowering season*.—Plants begin flowering about three months after planting; under garden conditions in The Netherlands, plants flower from spring to late autumn; plants can be flowered year-round in the greenhouse.

*Inflorescence longevity*.—Depending on the temperature, inflorescences last about two to four weeks on the plant; inflorescences persistent.

*Quantity of inflorescences*.—Freely flowering habit with about 16 inflorescences developing per plant during the flowering season.

*Inflorescence buds*.—Height: About 1.9 cm. Diameter: About 2 cm. Shape: Globular. Texture and luster: Moderately to densely pubescent; matte. Color: Close to 144B; towards the base, close to 146A; immature ray florets, close to 183D.

*Inflorescence size*.—Diameter: About 9.2 cm. Depth (height): About 2.9 cm. Diameter of disc: About 2.5 cm.

*Receptacles*.—Height: About 3 mm. Diameter: About 9 mm. Shape: Broadly rhomboidal. Color: Close to 145D.

*Ray florets*.—Quantity and arrangement: About 200 per inflorescence; ray florets arranged in about four outer whorls and two inner whorls of smaller ray florets. Orientation: Proximally, about 40° from vertical; distally, close to horizontal. Outer whorls of ray florets: Length: About 4.5 cm. Width: About 6 mm. Shape: Oblanceolate. Apex: Narrowly obtuse to bluntly acute. Base: Narrowly cuneate. Margin: Entire; not undulate. Texture and luster, upper surface: Smooth, glabrous; velvety; matte. Texture and luster, lower surface: Smooth, glabrous; slightly velvety; slightly carinate; slightly glossy. Color: When opening, upper surface: Close to a blend of 53A and 60A. When opening, lower surface: Close to 60C to lighter than 60C. Fully opened, upper surface: Close to 60A; venation, close to 60A; color does not change with subsequent development. Fully opened, lower surface: Close to 54A; towards the base, close to 54D; venation, similar to lamina colors; color does not change with subsequent development. Inner whorls of ray florets: Length: About 3.1 cm. Width: About 3.25 mm. Shape: Oblanceolate. Apex: Narrowly obtuse to bluntly acute. Base: Narrowly cuneate. Margin: Entire; not undulate. Texture and luster, upper surface: Smooth, glabrous; velvety; matte. Texture and luster, lower surface: Smooth, glabrous; slightly velvety; slightly carinate; slightly glossy. Color: When opening, upper surface: Close to a blend of 59C and 60A; apical edge, close to N155A. When opening, lower surface: Close to 63C to lighter than 63C. Fully opened, upper surface: Close to 60B; apical edge, close to N155A; venation, close to 60B; color does not change with subsequent development. Fully opened, lower surface: Close to 64D to lighter than 64D; venation, similar to lamina colors; color does not change with subsequent development.

*Disc florets*.—Quantity and arrangement: About 300 disc florets at center of the inflorescence arranged in about a ten-whorl spiral. Length: About 1.9 cm. Width: About 7 mm. Shape: Tubular with one or two narrow free lobes and one broader free lobe. Apex: Acute and recurved; upper 42.5%, free. Base: Lower 57.5%, fused. Margin, free lobes: Entire; not undulate. Texture, upper surface: Smooth, glabrous; moderately velvety; matte. Texture, lower surface: Smooth, glabrous; slightly velvety; slightly glossy. Color: When opening, inner surface: Apex, close to 60C, tipped with close to NN155A; mid-section and base, close to 157D. When opening, outer surface: Apex, close to 64C, tipped with close to NN155A; mid-section and base, close to 157D. Fully opened, inner surface: Apex, close to 64B, tipped with close to NN155A; mid-section and base, close to 157D. Fully opened, outer surface: Apex, close to 65D, tipped with close to NN155A; mid-section and base, close to 157D.

*Pappus*.—Quantity of hairs per floret: Numerous. Length: About 7 mm. Diameter: Less than 1 mm. Texture and luster: Soft; matte. Color: Close to 183D; towards the base, close to 150D.

*Phyllaries*.—Quantity and arrangement: About 80 per inflorescence arranged in about three whorls. Length: About 1.3 cm. Width (at base): About 2.25 mm. Shape: Linear. Apex: Narrowly acute. Base: Cuneate. Margin: Entire. Texture and luster, upper surface: Smooth, glabrous; moderately glossy. Texture and luster, lower surface: Moderately to densely pubescent; matte. Color, upper surface: Close to 144B; midvein, close to 143A. Color, lower surface: Close to 143B; towards the base, close to 137B.

*Peduncles*.—Length: About 40.7 cm. Diameter: Proximally, about 6 mm; distally, about 4 mm. Strength: Moderately strong. Angle: About 15° from vertical. Texture and luster: Moderately to densely pubescent; moderately glossy. Color: Close to 144A; distally, close to 146B.

*Reproductive organs*.—Androecium (present on disc florets only): Quantity per floret: Five. Filament length: About 6 mm. Filament color: Close to 155C. Anther shape: Linear; basifixed. Anther size: About 3 mm by 0.3 mm. Anther color: Close to 11A. Pollen amount: Scarce. Pollen color: Close to 11B. Gynoecium (present on ray and disc florets): Quantity per floret: One. Pistil length: About 1.2 cm. Stigma diameter: About 0.3 mm. Stigma shape: Cleft. Stigma color: Close to 155A. Style length: About 1.2 cm. Style color: Close to N155B. Ovary color: Close to 157A.

*Seeds and fruits*.—To date, seed and fruit production has not been observed on plants of the new *Gerbera*.

Pathogen & pest resistance: To date, resistance to pathogens and pests common to *Gerbera* plants has not been observed on plants of the new *Gerbera* grown under commercial production conditions.

Garden performance: Plants of the new *Gerbera* have been observed to have good garden performance and to tolerate temperatures ranging from about −5° C. to about 35° C. and to be cold hardy to USDA Hardiness Zone 7.

It is claimed:

1. A new and distinct *Gerbera* plant named 'MAJBUR20AA' as illustrated and described.

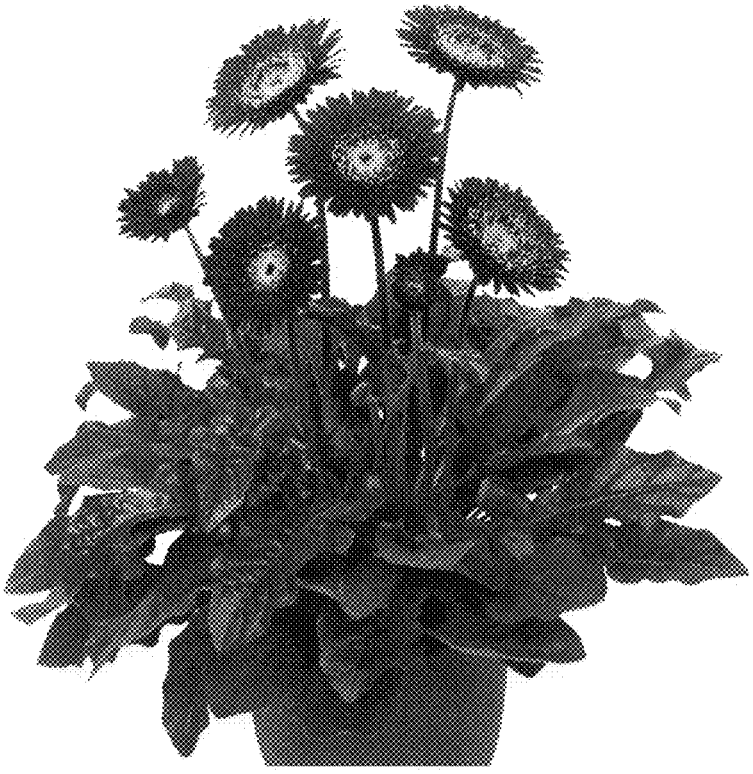

* * * * *